United States Patent [19]
Rhodes et al.

[11] Patent Number: 5,401,512
[45] Date of Patent: Mar. 28, 1995

[54] DELAYED RELEASE ORAL DOSAGE FORMS FOR TREATMENT OF INTESTINAL DISORDERS

[76] Inventors: John Rhodes, 25 Nantfawr Road, Cyncoed, Cardiff, South Glamorgan CF2 6JO; Brian K. Evans, 9 Merevale, The Common, Dinas Powis, South Glamorgain CF6 4HS, both of United Kingdom

[21] Appl. No.: 107,744
[22] PCT Filed: Feb. 21, 1992
[86] PCT No.: PCT/GB92/00318
§ 371 Date: Aug. 20, 1993
§ 102(e) Date: Aug. 20, 1993
[87] PCT Pub. No.: WO92/14452
PCT Pub. Date: Sep. 3, 1992

[30] Foreign Application Priority Data
Feb. 22, 1991 [GB] United Kingdom ............... 9103795

[51] Int. Cl.⁶ .................................................. A61K 9/58
[52] U.S. Cl. .................................... 424/458; 424/461; 424/462; 424/463
[58] Field of Search ............... 424/458, 462, 463, 461

[56] References Cited
U.S. PATENT DOCUMENTS
4,250,166 2/1981 Maekawa et al. .............. 424/419
5,260,071 11/1993 Lemelson ....................... 424/463
5,283,064 2/1994 Suzuki et al. ................... 424/463

FOREIGN PATENT DOCUMENTS
0040590 11/1981 European Pat. Off. .
0080341 6/1983 European Pat. Off. .
0366621 5/1990 European Pat. Off. .
0375063 6/1990 European Pat. Off. .
0386967 9/1990 European Pat. Off. .
3034929 2/1991 Japan .
2021407 12/1979 United Kingdom .
WO81/02671 10/1981 WIPO .
WO83/00435 2/1983 WIPO .

OTHER PUBLICATIONS
Roth et al 'hagers handbuch der pharmazeutischen praxis' 1971, Springer-verlag, Berlin Heidelbeerg New-York pp. 494–495, Nachbehandlungen von Gelatinkapseln.

Primary Examiner—Thurman K. Page
Assistant Examiner—Amy Hulina
Attorney, Agent, or Firm—Nixon & Vanderhye

[57] ABSTRACT

An orally administrable pharmaceutical dosage form for selectively administering a drug to the intestine comprises a plurality of enteric coated granules of the drug contained in an enterically coated capsule which releases the granules in the small intestine. The granules are preferably coated with a coating which remains intact until the coated granules reach at least the ileum and thereafter provide a sustained release of the drug in the colon. Suitable coating materials are selected from the Eudragit range of (meth)acrylate and (meth)acrylic and polymers. The invention has particular application to topically active drugs such as topically active steroids, bismuth salts and complexes, and especially, 5-amino-salicylic acid.

19 Claims, 1 Drawing Sheet

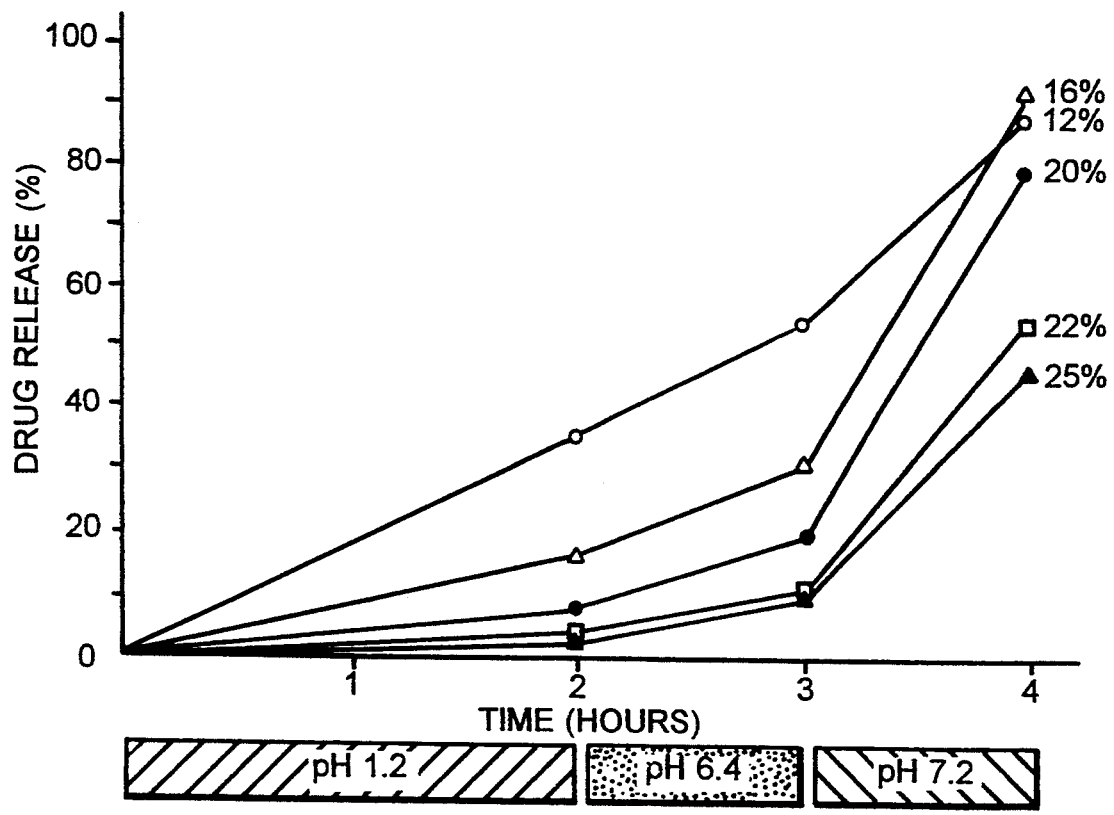

DELAYED RELEASE ORAL DOSAGE FORMS FOR TREATMENT OF INTESTINAL DISORDERS

The present invention relates to the administration of drugs to the intestine and has particular, but not exclusive, application to the treatment of colonic disorders by administration to the ileum and/or colon of drugs such as 5-amino-salicylic acid (hereinafter referred to as 5-ASA).

Treatment of diseases of the intestine usually requires the delivery of a drug to the affected site. When the disease is essentially confined to a specific part of the intestine, such as the colon in ulcerative colitis or Crohn's colitis, it is desirable to target administration of the drug to that part in order to provide and control optimum local concentration of the drug. In this connection, some drugs such as 5-ASA are absorbed or inactivated in the small intestine.

The formulation of a drug in a conventional enteric coated capsule or tablet merely prevents release of the drug until the alkaline environment of the small intestine is reached. The problem of targeting the drug to the colon in an effective and viable manner was not solved until the proposal by the present inventors to coat solid oral dosage forms with a thick coating of an anionic polymer of defined pH dissolution profile (see EP-A-0097651).

Several "delayed release" forms of orally administrable drugs have been proposed. The delayed release may result from the physical properties of the formulation or from the chemical and physical properties of a derivative of the drug. It is known to provide capsules and tablets with a coating which will disintegrate to release the drug gradually when the capsule or tablet has reached the acid environment of the stomach or the alkaline environment of the small intestine. Similarly, it is known to provide capsules and tablets with a coating permeable to the drug contained and through which the drug is gradually released.

It was proposed in GB-A-1219026 (published January 1971) to embed individual particles of a drug in a slowly disintegrating or slowly dissolving resin matrix having a particular dissolution profile to provide an orally administrable formulation for selectively administering the drug to the large intestine. The resin is selected such that the drug remains substantially protected within the resin matrix while the particles travel through the stomach and small intestine of a patient and that the drug is substantially completely exposed at the time the particles reach the large intestine. In particular, the nature and amount of the resin is selected so that when a quantity of the embedded drug is introduced into a Stoll-Gershberg disintegration apparatus, submerged in a simulated intestinal fluid (made in accordance with the U.S. Pharmacopoeia, Volume XVII, 1965 at page 919 but modified by containing no pancreatin), and operated as described in the patent specification, 2% to 12% of the drug dissolves within an hour of the introduction of the formulation into the fluid and 18% to 88% of the drug dissolves within three hours of said introduction. It is specifically stated that the resin is selected so that the dissolution rate of the drug is not pH dependent but is time dependent. The preferred resin is a high-viscosity grade modified vinyl acetate resin (available under the Registered Trade Mark "Gelva" C3-V30) and other specified resins are carboxylated polyvinyl acetates, polyvinyl/maleic anhydride copolymers, poly(methacrylic acid), ethylene/maleic anhydride copolymers, ethyl cellulose, methylacrylic acid/methyl methacrylate copolymers, waxes and mixtures thereof including mixtures with shellac. Tablets of the embedded particles coated with a standard coating solution containing cellulose-acetate-phthalate are reported.

It will be appreciated that the carrier system disclosed in GB-A-1219026 relies upon the rate of disintegration or dissolution of the resin as the preparation passes through the gastro-intestinal tract. The time dependency makes it impossible to limit administration of the drug to the colon because of large variations in the transit time in the gastro-intestinal tract, especially in the stomach, which occur between different patients and in the same patient from time to time. It would appear that the carrier system has not been satisfactory in practice because we are not aware of any relevant product presently available in the UK or elsewhere.

Anionic polymers have been known for many years to be of use in the preparation of coatings for capsules and to provide delayed or sustained release of an encapsulated drug. In particular, it has been known since at least 1974 to use for said coatings anionic copolymers of methacrylic acid and methacrylic acid methyl ester. Such a copolymer (available from Röhm Pharma GmbH, Darmstadt, Germany under the Registered Trade Mark "Eudragit" S) in which the ratio of free carboxyl groups to ester groups is approximately 1:2 had having a mean molecular weight of 135,000 is known to be insoluble in gastric juice and poorly soluble in intestinal juice while an analogous copolymer (available Röhm Pharma GmbH, Darmstadt, Germany under the Registered Trade Mark "Eudragit" L) differing only in so far as said ratio is approximately 1:1 also is insoluble in gastric juice but is readily soluble in intestinal juice. Prior to the invention of EP-A-0097651, said copolymers were usually employed to provide a coating of between 25 and 40 micrometers thick and the poorly soluble (in intestinal juice) copolymer usually is employed to reduce the dissolution (in intestinal juice) of the readily soluble copolymer. In general terms, except in connection with the invention of EP-A-0097651, anionic polymer coatings on oral dosage forms have been required to dissolve in aqueous medium at a pH below 7, usually between pH 5.5 and pH 7. Eudragit S dissolves above pH 7 but, as noted above, usually is employed in admixture with Eudragit L. As far as we are aware, said mixtures invariably dissolve below pH 7.

Salicylazosulphapyridine (also known as sulphasalazine or salazopyrin and hereinafter referred to as SASP) consists of sulphapyridine linked to a salicylate group by a diazo bond and has been used for decades in the treatment of colitis, Crohn's disease, idiopathic proctitis and chronic arthritis. Orally administered SASP is only absorbed to a limited extent before reaching the colon where azo-reductases produced by colonic bacteria act to split SASP into sulphapyridine and 5-ASA. Studies by A. K. A. Khan et al (The Lancet, Oct. 29 1977, p. 892) and others have shown the 5-ASA to be the pharmacologically active agent in the treatment of colonic disease with SASP. Sulphasalazine appears merely to act as a chemical carrier to deliver 5-ASA to the colon. When administered orally without the azo-bond joining them, sulphapyridine and 5-ASA are almost entirely absorbed from the small intestine before reaching the colon.

Several proposals have been made in recent years for the oral administration of 5-ASA avoiding using SASP in order to reduce the occurrence of side effects attributable to the sulphapyridine moiety. For example, in U.S. Pat. No. 4,190,716 (published February 1980), it was proposed to covalently bond the 5-ASA to a nonabsorbable pharmacologically acceptable organic polymer backbone comprising a plurality of aromatic rings by azo bonds bridging aromatic carbon atoms and the 5-position carbon of 5-ASA.

In GB-A-2021409 (published December 1979), it was proposed that 5-ASA should be administered concurrently or concomitantly with certain disodium cromoglycate-like compounds. Reference is made to formulating 5-ASA in sustained or controlled release form by coating some or all 5-ASA particles or granules thereof with a slowly soluble or digestible or semi-permeable layer of material such as beeswax, Carnauba wax, stearic or palmitic acids or cetyl alcohol. Reference also is made to coating tablets of the coated or uncoated 5-ASA with a continuous film of a material such as shellac or cellulose acetate phthalate which is resistant and impermeable to gastric secretions but susceptible to intestinal secretions. None of the coating materials specified or indicated in the specification are such as to prevent release of 5-ASA until the colon.

WO-A-81/02671 (published October 1981) proposed formulating 5-ASA in a sustained release tablet or enterosoluble tablet form and specifies ethyl cellulose as the preferred coating material. No coating materials other than cellulose derivatives are mentioned and it is granules, as distinct from tablets or other solid oral dosage forms, which are described as being coated. The coating is intended to provide sustained release of 5-ASA throughout the small and large intestine.

EP-A-0040590 (published November 1981) proposes coating a core of 5-ASA with a coating material comprising at least, (a) 10 to 85% by weight of an anionic carboxylic polymer soluble only above pH 5.5 and (b) 15 to 90% by weight of a water-soluble, quaternary ammonium substituted acrylic polymer. It is stated that the coating normally will be 3 to 60, preferably 10 to 30, micrometers thick and that partly methyl esterified methacrylic acid polymers are suitable anionic carboxylic polymers for use as component (a). In the Examples, Eudragit L and a mixture of Eudragit L and Eudragit S constitute the component (a) and in all cases the coatings dissolved below pH 7. The coated bodies of the EP-A-0040590 are subsequently included in dosage units which normally contain at least 10 coated bodies. The rationale of the coating system is stated to be that the change of pH from acid to neutral at the pylorus triggers a change in the physical condition of the coating so that 5-ASA is subsequently released after a predetermined time lag by which time the formulation should have reached the colon. Although time of passage through the small intestine is relatively constant, it still varies from 2 to 5 hours and hence the carrier system does not provide for reliable release of 5-ASA specifically in the colon.

EP-A-0097651 (published February 1983 as WO-A-8300435) disclosed that 5-ASA reliably can be administered specifically to the large intestine, especially the colon, by simply coating a solid oral dosage form with a 60 to 150 micrometers thick layer of an anionic polymer which is insoluble in gastric juice and in intestinal juice below pH 7 but soluble in colonic intestinal juice, whereby the oral dosage form remains intact until it reaches the colon. This carrier system differs from those previously disclosed in relation to 5-ASA in that dissolution or disintegration does not occur until entry of the coated dosage form into the colon. In particular, there is substantially no leaching out of the 5-ASA downstream of the colon in the normal patient. The carrier system is not limited to 5-ASA but can be used for other drugs, such as prednisolone methasulphobenzoate, which require to be targeted to the colon.

Although the 5-ASA formulation of EP-A-0097651 has found widespread and increasing use in the treatment of ulcerative colitis or Crohn's colitis, there are occasions upon which it would be desirable to avoid the release of a large bolus of 5-ASA or other drug in the colon and to deliver the drug in smaller quantities instead to give more of a plateau release than the rapid peak absorption caused by bolus releases and to reduce the risk of local irritation. Further, it is desirable to provide a more flexible release system which would permit targeted release in the small intestine instead of in the colon. Accordingly, we have investigated the possibility of alternative formulations for targeting drugs to the intestine. As a result of those investigations, we have found that the drug can successfully be targeted by replacing the coated oral dosage form of EP-A-0097651 with individually coated granules within an enteric coated capsule.

In its broadest aspect, the present invention provides an orally administrable pharmaceutical dosage form for selectively administering a drug to the intestine comprising a plurality of granules of the drug contained in a capsule, characterized in that said granules and said capsule are coated with the same or different coating material which dissolves in the intestine.

BRIEF DESCRIPTION OF THE DRAWING

FIG. 1 shows the percent of 5-ASA released from coated granules comprised of 12%, 16%, 20%, 22% and 25% of the coating mixture when the granules were exposed to pH 1.2 for 2 hours, then pH 6.4 for 1 hour and finally pH 7.2 for 1 hour.

According to a preferred embodiment, the present invention provides an orally administrable pharmaceutical dosage form for selectively administering a drug to the large intestine comprising a plurality of granules of the drug contained in an enterically coated capsule which releases the granules in the small intestine, characterized in that said granules are coated with a coating which remains substantially intact until the coated granules reach at least the ileum and, preferably, thereafter provides a sustained release of the drug in the colon.

According to an especially preferred embodiment of the present invention, there is provided an orally administrable pharmaceutical dosage form for selectively administering a drug to the colon comprising a plurality of granules of the drug contained in an enterically coated capsule which releases the granules in the small intestine, characterized in that said granules are coated with a coating material comprising an anionic polymer which is insoluble in gastric juice and in intestinal juice below pH 7 but is soluble in colonic intestinal juice whereby the coating on the released coated granules remains substantially intact until the granules reach at least the ileum and, preferably, thereafter provides a sustained release of the drug in the colon.

Although the invention has particular application to 5-ASA, it can be used to target any desired drug, especially a topically active drug, to the intestine. In particular, it has application to the administration of topically active steroids such as prednisolone metasulphobenzoate to the ileum and/or colon. Other drugs which can be administered by the invention include bismuth salts or complexes, for example bismuth-carboner complexes. The relevant drug will be present in the dosage form of the invention in suitable unit dose amounts. Said amounts will be known or readily ascertainable by those skilled in the art. In many cases, said amounts are likely to be less than those presently administered by conventional delayed or sustained release dosage forms because of the high organ specificity of the dosage form of the present invention.

The drug is present in the dosage form of the invention in granular form. Suitably the granules are 0.25 to 4 mm, usually 0.25 to 2.5 mm, especially 0.4 to 1.5 mm and particularly about 0.6 mm, diameter.

The coating can be applied to the granules by any suitable known coating technique. In particular, conventional coating techniques such as spray or pan coating can be employed. (See, eg, "Film coatings on acrylic resin basis for dosage forms with controlled drug release" Pharma International ½ (1975) 3.) Preferably, the coating is applied from aqueous suspension.

The granular coating material can be any suitable coating, e.g. cellulose acetate phthalate, hydroxypropyl methyl cellulose phthalate, ethyl cellulose or polyvinyl acetate phthalate but the preferred coating material is an anionic polymer, especially one having the dissolution profile specified in EP-A-0097651, optionally in admixture with a neutral insoluble but permeable polymer. The presently preferred anionic polymers are anionic carboxylic polymers, i.e. polymers in which the anionic groups are at least predominantly free carboxylic and/or esterified carboxylic groups. It is particularly preferred that the anion polymers should be acrylic polymers and the presently most preferred polymers are partly methyl esterified methacrylic acid polymers in which the ratio of free acid groups to ester groups is about 1:1 (i.e. Eudragit L), or especially, about 1:2 (i.e. Eudragit S). The neutral insoluble but permeable polymers preferably are acrylic ester polymers, especially methylmethacrylate ester copolymers with ethylacrylate. Suitably, the molecular ratio of anionic polymer to neutral polymer is in the range 5:1 to 1:5, especially 3:1 to 1:3, most preferably 1:1 to 1:3.

The thickness of coating required on the granules will depend upon the dissolution profile of the particular coating materials and possibly also upon the dissolution profile of the enteric coating on the capsule. However, it is well within the ability of the man of average skill in the art to determine by trial-and-error experimentation the optimum thickness of a particular coating required for a particular dosage form of the invention. When using an aqueous dispersion of a partly methyl esterified methacrylic acid polymer of the Eudragit S type admixed with a methylmethacrylate/ethylacrylate copolymer, the amount of coating material usually will be between 15 and 30% dry weight based on the uncoated granule) with 20 to 25% being preferred.

The coating can, and usually will, contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate, although the presence of such a plasticiser may not be necessary when using an aqueous suspension for coating.

Usually, the capsule into which the coated granules are loaded will be a soft or, preferably, hard gelatin capsule although other capsules which will dissolve in the small intestine can be used. The capsule is coated with an enteric coating which will protect it during passage through the stomach. Any conventional enteric coating material which is soluble in the small intestine can be used, e.g. cellulose acetate phthalate, hydroxy propylmethyl cellulose phthalate or initially ethyl cellulose followed by polyvinyl acetate phthalate, but it is preferred to use an anionic polymer having an appropriate dissolution profile. The presently preferred polymers are anionic carboxylic polymers, i.e. polymers in which the anionic groups are at least predominantly free carboxylic and/or esterified carboxylic groups. It is particularly preferred that the polymers should be acrylic polymers and the presently most preferred polymers are partly methyl esterified methacrylic acid polymers in which the ratio of free acid groups to ester groups is about 1:1 (i.e. Eudragit L).

The enteric coating can, and usually will contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate.

Conventional coating techniques such as spray or pan coating are employed to apply the enteric coating (See for example D. Dreher "Film coatings on acrylic resin basis for dosage forms with controlled drug release" Pharma International ½ (1975) 3.)

The following non-limiting Examples are provided to illustrate the dosage forms of the invention:

EXAMPLE 1

Granules of size in the range 0.5–2.1 mm were prepared by dry compacting and subsequently sieving a tablet mass containing 5-ASA. The granules were then spray coated with an aqueous suspension to provide a 20% or 25% dry weight gain based on uncoated granule weight of a mixture of Eudragit S100 and Eudragit NE 30 D (Röhm Pharma GmbH, Darmstadt, Germany) in the ratio of 3:7. Eudragit S100 is a copolymer of methacrylic acid and methylmethacrylate in the ratio of 1:2 in powder form and Eudragit NE 30 D is a 30% aqueous dispersion of a copolymer of ethylacrylate and methylmethacrylate in the ratio 2:1.

The resulting granules had the following formulations:

| Material | 20% coating | 25% coating |
| --- | --- | --- |
| 5-ASA | 59.1 g | 55.8 g |
| Lactose | 11.3 g | 10.7 g |
| Povidone (ie. PVP) | 1.3 g | 1.2 g |
| Explotab (Na starch glycolate) | 2.7 g | 2.5 g |
| Mg stearate | 0.9 g | 0.9 g |
| Talc | 9.2 g | 10.6 g |
| Eudragit S100 | 4.6 g | 5.4 g |
| Eudragit NE 30 D | 10.8 g | 12.7 g |
| Antifoam emulsion SE 2 | 0.1 g | 0.1 g |
| Total | 100.0 g | 100.0 g |

Each of the batches of coated granules were separately packed into size 00 hard gelatin capsules (LOK- CAP, Eli Lilly) in an amount of 400 mg granules per capsule. The capsules were then spray coated with 150 ml per capsule of a coating solution of the following formula:

| | |
|---|---|
| Eudragill L powder | 3 g |
| Diethyl phthalate | 0.75 ml |
| Silicone fluid 200 cs | 0.75 ml |
| Acetone | to 100 ml. |

Seven healthy volunteers were then each given blind on three separate occasions a single dose consisting of (a) 8 tablets of enteric coated 500 mg sulphasalazine tablets, (b) 8 of the enteric coated capsules containing the 20% Eudragit coated 5-ASA granules, and (c) 8 of the enteric coated capsules containing the 25% Eudragit coated 5-ASA granules. The serum levels of 5-ASA and N-acetyl-5-ASA at various times following administration were measured together with the total urinary excretion of 5-ASA and N-acetyl-5-ASA. The mean of the values recorded are set forth in the following Tables 1 to 3. In each case the values are given to three significant figures with 0 representing less than 2 ng/ml. The following abbreviations are used:

$T_{max}$=time for the maximum serum concentration in hours, median and interquartials ranges $C_{max}$=maximum serum concentration attained in ng/ml AUC=area under the serum concentration time curve (50 h; ng.h/ml)

$T_{half}$=estimated biological half life of elimination

KE=estimated first order in elimination rate constant

TABLE 1

Mean serum levels of 5-ASA (ng/ml) in 7 volunteers following administration of the three different drug formulations.

| Time (h) | 5-ASA 20% | Sulphasalazine | 5-ASA 25% |
|---|---|---|---|
| 0 | 0 ± 0 | 0 ± 0 | 0 ± 0 |
| 2 | 9 ± 7 | 0 ± 0 | 1 ± 0 |
| 3.5 | 102 ± 88 | 0 ± 0 | 70 ± 40 |
| 5 | 227 ± 142 | 7 ± 4 | 155 ± 65 |
| 6.5 | 153 ± 101 | 30 ± 19 | 54 ± 22 |
| 8 | 193 ± 108 | 30 ± 15 | 73 ± 37 |
| 9.5 | 143 ± 104 | 49 ± 19 | 37 ± 15 |
| 12 | 17 ± 7 | 61 ± 29 | 17 ± 9 |
| 15 | 38 ± 23 | 99 ± 31 | 22 ± 15 |
| 26 | 56 ± 28 | 43 ± 23 | 4 ± 3 |
| 36 | 19 ± 10 | 12 ± 9 | 10 ± 10 |
| 50 | 6 ± 4 | 1 ± 1 | 14 ± 14 |
| $T_{max}$ | 6.5 (3.1–13.6) | 15 (6.5–15) | 5 (3.8–6.9) |
| $C_{max}$ | 400 ± 142 | 102 ± 32 | 215 ± 54 |
| AUC | 2480 ± 450 | 1610 ± 664 | 1080 ± 299 |
| $T_{half}$ | 7.2 ± 3.0 | 19.4 ± 12.9 | 1.7 ± 0.6 |
| KE | 0.2 ± 0.1 | 0.1 ± 0.04 | 0.7 ± 0.3 |

TABLE 2

Mean serum levels of N-Ac-5-ASA (ng/ml) in 7 volunteers following administration of the three different drug formulations.

| Time (h) | 5-ASA 20% | Sulphasalazine | 5-ASA 25% |
|---|---|---|---|
| 0 | 0 ± 0 | 0 ± 0 | 0 ± 0 |
| 2 | 90 ± 53 | 0 ± 0 | 9 ± 9 |
| 3.5 | 363 ± 267 | 18 ± 17 | 258 ± 113 |
| 5 | 756 ± 388 | 97 ± 52 | 473 ± 174 |
| 6.5 | 714 ± 280 | 186 ± 84 | 410 ± 93 |
| 8 | 650 ± 228 | 343 ± 134 | 453 ± 77 |
| 9.5 | 545 ± 205 | 391 ± 117 | 436 ± 69 |
| 12 | 417 ± 119 | 556 ± 88 | 440 ± 151 |
| 15 | 425 ± 184 | 763 ± 151 | 355 ± 86 |
| 26 | 590 ± 124 | 505 ± 130 | 182 ± 40 |
| 36 | 389 ± 140 | 285 ± 117 | 169 ± 72 |
| 50 | 188 ± 92 | 191 ± 133 | 125 ± 92 |
| $T_{max}$ | 26 (6.1–26) | 15 (13.3–17.8) | 8 (5–9.5) |
| $C_{max}$ | 1420 ± 296 | 841 ± 153 | 822 ± 112 |
| AUC | 21300 ± 2270 | 18400 ± 3820 | 11800 ± 2090 |
| $T_{half}$ | 10.8 ± 2.4 | 60.1 ± 50.1 | 12.8 ± 4.5 |
| KE | 0.1 ± 0.02 | 0.1 ± 0.02 | 0.1 ± 0.01 |

TABLE 3

Mean urinary excretion of 5-ASA and N-Ac-5-ASA (ng/ml) in 7 volunteers following administration of the three different drug formulations.

| | 5-ASA 20% | Sulphasalazine | 5-ASA 25% |
|---|---|---|---|
| 5-ASA | 5.35 ± 2.59 | 0 ± 0 | 1.40 ± 0.35 |
| N-AC-5-ASA | 194 ± 24 | 170 ± 35 | 129 ± 29 |

As can be seen from the tables, the mean serum concentrations of 5-ASA were lower than those of its acetylated metabolite following oral ingestion of each of the three preparations. Peak concentrations of serum 5-ASA and N-acetyl-5-ASA occurred earlier with both 5-ASA capsules compared with sulphasalazine. However, following administration of the capsule containing 20% Eudragit coated 5-ASA there was a second rise in both serum 5-ASA and N-acetyl-5-ASA at 15 h, with levels thereafter similar to those after sulphasalazine.

These results suggest that more 5-ASA is available for earlier absorption after ingestion of the 5-ASA capsules than after sulphasalazine. The early peaks after both capsules correspond to drug absorbed in the small bowel following dissolution of the capsule coated with Eudragit-L. Other granules reach the terminal ileum and proximal colon where, at a pH above 7, further drug release would be expected. This accounts for the second rises of serum 5-ASA and N-acetyl-5-ASA seen 15 hours after ingestion of the capsule containing 20% Eudragit coated 5-ASA.

Release of free 5-ASA in the proximal small bowel, or substantial release of the drug in one region of the ileal or ileo-caecal area, can lead to high peak serum levels of 5-ASA and its metabolites, leaving less drug available for topical action in the colon. The coated granules/coated capsules of this invention deliver 5-ASA to the distal small bowel, limit sudden release of free compound, and make the drug available for absorption over a longer period as with sulphasalazine.

EXAMPLE 2

The granule coating procedure of Example 1 was repeated using 12%, 16%, 20%, 22% and 25% of the coating mixture. The dissolution of the coated granules was examined by a standard flow-through cell dissolution system which automatically changed the pH at pre-determined time intervals. The coated granules were exposed to pH 1.2 for 2 h, then pH 6.4 for 1 h, and finally pH 7.2 for 1 h. 5-ASA was measured spectrophotometrically and the results are shown in FIG. 1.

As can be seen, the pH influenced the drug release from granules coated with at least 16% dry lacquer substance.

With 20% of dry lacquer substance, the amount of 5-ASA release after 2 h at pH 1.2 was 7.8%, compared with 18.5% at pH 6.4 for 1 h, and 77.8% after 1 h at pH 7.2 (accumulated percentages); with 25% of dry lacquer substance the respective percentage 5-ASA release was 3.6%, 10% and 48%.

We claim:

1. An orally administrable pharmaceutical dosage form for selectively administering a drug to the intestine comprising a plurality of granules of the drug contained in an enterically coated capsule which releases the granules in the small intestine, wherein said granules are coated with a coating which remains substantially intact until the coated granules reach at least the ileum.

2. An orally administrable pharmaceutical dosage form for selectively administering a drug to the intestine comprising a plurality of granules of the drug contained in an enterically coated capsule which releases the granules in the small intestine, wherein said granules are coated with a coating comprising an anionic polymer which is insoluble in gastric juice and in intestinal juice below pH 7 but is soluble in colonic intestinal juice whereby the coating on the released coated granules remains substantially intact until the granules reach at least the ileum.

3. An orally administrable pharmaceutical dosage form for selectively administering a drug to the intestine comprising a plurality of granules of the drug contained in a capsule coated with a coating comprises a partly methyl esterified methacrylic acid polymer having a ratio of free acid groups to ester groups of about 1:1 whereby the granules are released in the small intestine, wherein said granules are coated with a coating comprising a partly methyl esterified methacrylic acid polymer having a ratio of free acid groups to ester groups of about 1:2 and which is insoluble in gastric juice and in intestinal juice below pH 7 but is soluble in colonic intestinal juice whereby the coating on the released coated granules remains substantially intact until the granules reach at least the ileum.

4. An orally administrable pharmaceutical dosage form for selectively administering a drug, selected from the group consisting of 5-aminosalicylic acid and a pharmaceutically acceptable salt or ester thereof; topically active steroids; and bismuth salts and complexes, to the intestine comprising a plurality of granules of the drug contained in an enterically coated capsule which releases the granules in the small intestine, wherein said granules are coated with a coating which remains substantially intact until the coated granules reach at least the ileum.

5. An orally administrable pharmaceutical dosage form for selectively administering a drug, selected from the group consisting of 5-aminosalicylic acid and a pharmaceutically acceptable salt or ester thereof; topically active steroids; and bismuth salts and complexes, to the intestine comprising a plurality of granules of the drug contained in an enterically coated capsule which releases the granules in the small intestine, wherein said granules are coated with a coating comprising an anionic polymer which is insoluble in gastric juice and in intestinal juice below pH 7 but is soluble in colonic intestinal juice whereby the coating on the released coated granules remains substantially intact until the granules reach at least the ileum.

6. An orally administrable pharmaceutical dosage form for selectively administering a drug, selected from the group consisting of 5-aminosalicylic acid and a pharmaceutically acceptable salt or ester thereof; topically active steroids; and bismuth salts and complexes, to the intestine comprising a plurality of granules of the drug contained in a capsule coated with a coating comprises a partly methyl esterified methacrylic acid polymer having a ratio of free acid groups to ester groups of about 1:1 whereby the granules are released in the small intestine, wherein said graules are coated with a coating comprising a partly methyl esterified methacrylic acid polymer having a ratio of free acid groups to ester groups of about 1:2 and which is insoluble in gastric juice and in intestinal juice below pH 7 but is soluble in colonic intestinal juice whereby the coating on the released coated granules remains substantially intact until the granules reach at least the ileum.

7. A dosage form as claimed in claim 1, wherein said, granule coating provides a sustained release of the drug in the colon.

8. A dosage form as claimed in claim 2, wherein said granule coating provides a sustained release of the drug in the colon.

9. A dosage form as claimed in claim 1, wherein said drug is 5-aminosalicylic acid or a pharmaceutically acceptable salt or ester thereof.

10. A dosage form as claimed in claim 1, wherein the drug is a topically active steroid or a bismuth salt or complex.

11. A dosage form as claimed in claim 2, wherein the anionic polymer is a partly methyl esterified methacrylic acid polymer.

12. A dosage form as claimed in claim 11, wherein the partly methyl esterified methacrylic acid polymer has a ratio of free acid groups to ester groups of about 1:2.

13. A dosage form as claimed in claim 1, wherein the capsule is a hard gelatin capsule.

14. A dosage form as claimed in claim 1, wherein the capsule is coated with an anionic carboxylic acrylic polymer.

15. A dosage form as claimed in claim 14, wherein the capsule coating is a partly methyl esterified methacrylic acid polymer.

16. A dosage form as claimed in claim 15, wherein the capsule coating is a partly methyl esterified methacrylic acid polymer having a ratio of free acid groups to ester groups of about 1:1

17. A method of treating ulcerative colitis or Crohn's disease comprising orally administering to a person suffering therefrom a pharmaceutically effective amount for the treatment of ulcerative colitis or Crohn's disease of a drug selected from the group consisting of 5-aminosalicylic acid and a pharmaceutically acceptable salt or ester thereof; topically active steroids; and bismuth salts and complexes, in an pharmaceutical dosage form comprising a plurality of granules of the drug contained in an enterically coated capsule which releases the granules in the small intestine, wherein said granules are coated with a coating which remains substantially intact until the coated granules reach at least the ileum.

18. A method of treating ulcerative colitis or Crohn's disease comprising orally administering to a person suffering therefrom a pharmaceutically effective amount for the treatment of ulcerative colitis or Crohn's disease of a drug selected from the group consisting of 5-aminosalicylic acid and a pharmaceutically acceptable salt or ester thereof; topically active steroids; and bismuth salts and complexes, in a pharmaceutical dosage form comprising a plurality of granules of the drug contained in an enterically coated capsule which releases the granules in the small intestine, wherein said granules are coated with a coating comprising an anionic polymer which is insoluble in gastric juice and in intestinal juice below pH 7 but is soluble in colonic intestinal juice whereby the coating on the released coated granules remains substantially intact until the granules reach at least the ileum.

19. A method of treating ulcerative colitis or Crohn's disease comprising orally administering to a person suffering therefrom a pharmaceutically effective amount for the treatment of ulcerative colitis or Crohn's disease of a drug selected from the group consisting of 5-aminosalicylic acid and a pharmaceutically acceptable salt or ester thereof; topically active steroids; and bismuth salts and complexes, in a pharmaceutical dosage form comprising a plurality of granules of the drug contained in a capsule coated with a coating comprises a partly methyl esterified methacrylic acid polymer having a ratio of free acid groups to ester groups of about 1:1 whereby the granules are released in the small intestine, wherein said granules are coated with a coating comprising a partly methyl esterified methacrylic acid polymer having a ratio of free acid groups to ester groups of about 1:2 and which is insoluble in gastric juice and in intestinal juice below pH 7 but is soluble in colonic intestinal juice whereby the coating on the released coated granules remains substantially intact until the granules reach at least the ileum.

* * * * *